United States Patent [19]

Berguer

[11] 4,309,776
[45] Jan. 12, 1982

[54] INTRAVASCULAR IMPLANTATION DEVICE AND METHOD OF USING THE SAME

[76] Inventor: Ramon Berguer, 5865 Bloomfield Glens, West Bloomfield, Mich. 48033

[21] Appl. No.: 149,484

[22] Filed: May 13, 1980

[51] Int. Cl.³ .................. A61F 1/00; A61F 1/24; A61M 5/00
[52] U.S. Cl. .................................................. 3/1; 3/1.4; 128/1 R; 128/260
[58] Field of Search ............... 3/1, 1.4; 128/260, 1 R, 128/DIG. 14

[56] References Cited

U.S. PATENT DOCUMENTS

| | | | |
|---|---|---|---|
| 3,093,831 | 6/1963 | Jordan | 3/1 |
| 3,279,996 | 10/1966 | Long, Jr. et al. | 3/1 UX |
| 3,765,414 | 10/1963 | Arlen | 3/1 X |
| 3,948,254 | 4/1976 | Zaffaroni | 3/1 X |
| 4,101,984 | 7/1978 | MacGregor | 3/1 X |

Primary Examiner—Ronald L. Frinks
Attorney, Agent, or Firm—Whittemore, Hulbert & Belknap

[57] ABSTRACT

An intravascular device having a chamber for containing transplanted cells. The device is adapted to be implanted in a wall of a blood vessel with a porous chamber-forming wall of the chamber providing an interface between the cells in the chamber and the blood in the vessel. The chamber-forming wall has a pore size permitting continuous diffusion of hormonal components therethrough but blocking the diffusion of cells. The device may also be implanted between an artery and a vein in a wall of each so as to act as a sieve between the artery and vein subject to the differential pressure therebetween. A method is also disclosed for employing the device to introduce hormonal components into the blood stream.

15 Claims, 4 Drawing Figures

INTRAVASCULAR IMPLANTATION DEVICE AND METHOD OF USING THE SAME

This invention relates generally to an intravascular implantation device and method of using the same, and refers more particularly to a device having a chamber for containing transplanted cells and adapted to be implanted in a wall of a blood vessel, or to be implanted between an artery and a vein in a wall of each, for the purpose of introducing hormonal components into the blood stream of a human being.

BACKGROUND AND SUMMARY

Previous work has been done in the field of enclosed cell implantation or transplantation using Millipore chambers. These chambers were generally implanted in the peritoneal cavity.

The present invention involves use of a blood vessel as an implantation site in order to provide the closest proximity to plasma and to enhance diffusion by taking advantage of intravascular pressure. The material of which the chamber-forming device is made must be tolerated in a blood vessel without causing thrombosis and should permit the choice of various degrees of porosity. Expanded polytetrafluoroethylene (PTFE) fulfills both of these requirements.

The device may be implanted as a "button" in the wall of a blood vessel (artery or vein) in which case it would be subject to the pressure gradient between the blood vessel and tissue. The device may also be implanted between an artery and a vein to serve as a "sieve" between the two in an arteriovenous fistula. This latter approach has the advantages of a greater pressure differential across the chamber and of providing greater filtration surface area.

The foregoing and other objects of the invention will become apparent as the following description proceeds, especially when considered with the accompanying drawings.

DETAILED DESCRIPTION

Figure 1:
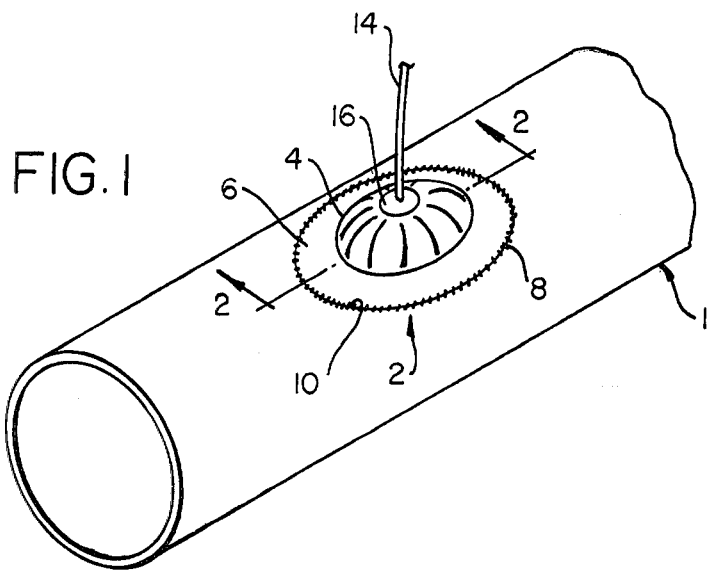
FIG. 1 is a perspective view of a chamber-forming device of my invention shown implanted in a wall of a blood vessel.
Figure 2:
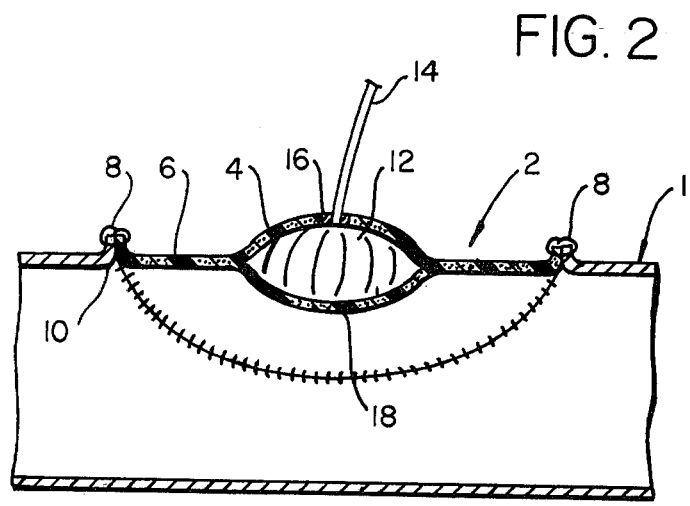
FIG. 2 is a longitudinal sectional view taken on the line 2—2 in FIG. 1.

Referring now more particularly to the drawings and especially to FIGS. 1 and 2 thereof, the numeral 1 designates a human blood vessel (vein or artery) and 2 designates my chamber-forming device shown implanted as a "button" in the wall of the blood vessel.

The device 2 is similar in appearance to a so-called flying saucer. It comprises a hollow capsule 4 which preferably is in the form of a considerably flattened and somewhat elongated body, having a peripheral flange 6 about a line of maximum circumference. The edge of the flange is shown attached by 360° of stitching 8 to the margin of an opening 10 in the blood vessel with the major axis of the device extending lengthwise of the blood vessel. The hollow capsule 4 defines an essentialy closed chamber 12 adapted to contain transplanted hormone-producing cells. A tube 14 is provided for the injection or aspiration of cells to the chamber. One end of the tube 14 is attached to the wall of the capsule by a flange 16; the other end is plugged and lies in the tissues of the body in the neighborhood of the implanted device where it can be reached by means of an operation for the purpose of aspirating or injecting these cells into the chamber without disturbing the chamber itself.

The device 2 is formed of a porous, biocompatible, non-thrombus-inducing, flexible material. The entire device is made of porous material because only porous materials can be sewn into blood vessels and heal without thrombus formation. In addition to this porosity requirement for healing purposes, there is another specific requirement for porosity that has to do with filtration and this applies to that portion of the capsule that filters the blood from the vessel into the chamber of the capsule, namely, the chamber-forming wall or membrane 18, which provides an interface between the cells in the chamber 12 and the blood in the blood vessel 1. This filtration wall or membrane 18 has a porosity such that substances in the blood (a plasma filtrate) may cross from the blood to the inside of the chamber for nutrition and stimulation of hormonal production, and also so that hormonal secretion by the cells inside the chamber may cross from within the chamber to the blood coursing through the blood vessel. The pore size of the chamber-forming wall or membrane 18 is such as to permit continuous diffusion of hormonal components but block diffusion of cells. To this end, these pores will have a diameter of about 0.2 microns to about 25 microns. Those portions of the device 2 other than the chamber-forming wall or membrane 18, will have different porosity in the neighborhood of 25 microns or more and will probably be reinforced in all parts not in contact with the blood so as to allow only minimal filtration. Those portions of the device not in contact with the blood in the blood vessel will, soon after implantation (within about 30–60 days) become effectively non-porous by macrophage migration (encapsulation by scar) so as to block diffusion of cellular and hormonal components.

The material from which the device 2 is made is preferably porous expanded polytetrafluoroethylene (PTFE). The tube 14 and flange 16 are formed of a non-porous material preferably PTFE.

The filtering wall 18 should be as thin as possible, yet of sufficient thickness to have enough strength to withstand arterial stress. The other portions of the device may be somewhat thicker and sturdier to facilitate attachment and to discourage cell and plasma diffusion.

In use, the device 2 is implanted by attachment to a blood vessel in the manner shown in FIGS. 1 and 2 and described above. Cells are injected into the chamber 12 through tube 14. Thereafter, blood substance may filter through the wall 18 of the capsule for nutrition and stimulation of hormonal production within the chamber, and hormonal secretion by the cells inside the chamber may filter through the wall 18 to the blood. Even though initially porous, those walls and surfaces of the device not in contact with the blood will eventually become non-porous by macrophage migration and collagen deposition (scar formation).

Figure 3:
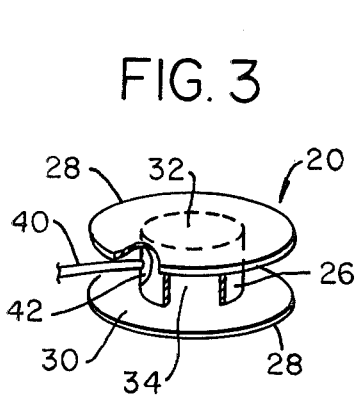
FIG. 3 is a perspective view of a chamber-forming device of modified construction, with parts broken away and in section.
Figure 4:
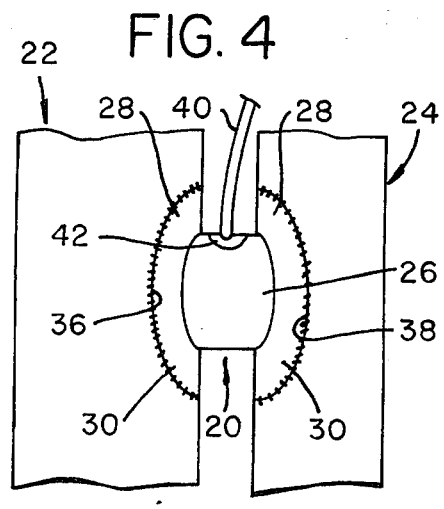
FIG. 4 is an elevational view showing the device of FIG. 3 implanted as a "sieve" between an artery and a vein as an arteriovenous fistula.

FIGS. 3 and 4 show a device 20 of modified construction, adapted to be implanted between an artery 22 and a vein 24 of a human. The device 20 comprises a hollow cylinder 26, the ends of which are closed by discs 28 which have flanges 30 that project radially outwardly beyond the cylinder 26. The cylinder and flanges may be slightly oblong, if desired. The cylinder 26 and the portions 32 of the discs 28 closing the ends of the cylinder form a capsule which defines a closed chamber 34 adapted to contain the transplanted cells. The portions 32 of the discs provide filtration walls or membranes. The edges of the flanges 30 are attached by 360° of stitching to openings 36 and 38 in the artery 22 and vein 24 respectively. If the device is oblong, its major axis extends lengthwise of the blood vessels.

A tube 40 is provided for the injection or aspiration of cells and has one end attached to the cylinder 26 by a small flange 42. The other end terminates in the tissues in the neighborhood of the device so that it may be accessed through a small operation for injecting cells or removing them from the chamber.

The device 20 may be formed of the same porous, flexible material having the same thickness as the device 2 previously described. Pore sizes of the filtration walls or membranes 32 and of the other portions of the device 20 are the same as for the corresponding portions of the device 2. The tube 40 and flange 42 are preferably made of non-porous PTFE. Further as was the case with the embodiment first described, those walls and surfaces of the device not in contact with the blood in the blood vessels become effectively non-porous by macrophage migration and collagen deposition (scar formation) shortly after transplantation to block diffusion of cellular and hormonal components.

In use of the device when implanted as in FIGS. 3 and 4, cells may be injected into chamber 34 through tube 40. The device acts as a "sieve" between the artery 22 and vein 24 in an arteriovenous fistula. One chamber-forming wall 32 forms an interface between the cells in chamber 34 and the blood in artery 22, and the other chamber-forming wall 32 forms an interface between the cells in the chamber and the blood in vein 24. Thus, there are two filtering walls enabling blood substances to cross into the chamber and hormonal components to cross into the blood but blocking diffusion of cells. Advantages of the embodiment of FIGS. 3 and 4 over that of FIGS. 1 and 2 include greater pressure differential between an artery and a vein and greater filtrating surface area.

I claim:

1. An intravascular device having a chamber for containing transplanted cells and having outwardly extending peripheral flange means designed and shaped for suturing in an opening made in the wall of a blood vessel with a porous chamber-forming wall thereof providing an interface between the cells in the chamber and the blood in the vessel, said porous chamber-forming wall having a pore size permitting continuous diffusion of hormonal components therethrough but blocking the diffusion of cells.

2. An intravascular device having a chamber for containing transplanted cells and adapted to be implanted between an artery and a vein and having outwardly extending peripheral flange means designed and shaped for suturing in an opening made in a wall of each with a porous chamber-forming wall of said device providing an interface between the cells in said chamber and the blood in the artery and another porous chamber-forming wall of said device providing an interface between the cells in said chamber and the blood in the vein, said porous chamber-forming walls each having a pore size permitting continous diffusion of hormonal components therethrough but blocking the diffusion of cells so that said device acts as a sieve between said artery and vein subject to the differential pressure therebetween.

3. An intravascular device as defined in claim 1 or 2, wherein the pores in said chamber-forming wall or walls have a diameter in a range on the order of about 0.2 microns to 25 microns.

4. An intravascular device as defined in claim 1 or 2 wherein said device is made of a biocompatible, non-thrombus-inducing material.

5. An intravascular device as defined in claim 1 or 2, wherein said device is made of polytetrafluoroethylene.

6. An intravascular device as defined in claim 1 or 2, wherein other walls of said device not in contact with the blood will become effectively non-porous once they are healed and thereby block diffusion of cellular and hormonal components.

7. An intravascular device as defined in claim 1, wherein said device is in the form of a considerably flattened and somewhat elongated hollow body, said flange means comprising a peripheral flange on said body about a line of maximum circumference thereof for attachment to a wall of the blood vessel.

8. An intravascular device as defined in claim 2, wherein said device is in the form of a hollow body, said flange means comprising annular flanges on said body in spaced relation to one another for attachment respectively to a wall of the artery and a wall of the vein.

9. An intravascular device as defined in claim 1 or 2, including a tube communicating with said chamber for the introduction of hormone-producing cells.

10. A method for introducing hormonal components into the blood stream comprising implanting in a wall of a blood vessel a device having a chamber containing transplanted cells with a porous chamber-forming wall thereof providing an interface between the cells in the chamber and the blood in the vessel, said porous chamber-forming wall having a pore size permitting continuous diffusion of hormonal components therethrough but blocking the diffusion of cells.

11. A method for introducing hormonal components into the blood stream comprising implanting between an artery and a vein in a wall of each a device having a chamber containing transplanted cells with a porous chamber-forming wall of said device providing an interface between the cells in said chamber and the blood in the artery and another porous chamber-forming wall of said device providing an interface between the cells in said chamber and the blood in the vein, said porous chamber-forming walls each having a pore size permitting continuous diffusion of hormonal components therethrough but blocking the diffusion of cells so that said device acts as a sieve between said artery and vein subject to the differential pressure therebetween.

12. A method as defined in claim 10 or 11, wherein the pores in said chamber-forming wall or walls have a diameter in a range on the order of about 0.2 microns to 25 microns.

13. A method as defined in claim 10 or 11, wherein said device is made of a biocompatible, non-thrombus-inducing material.

14. A method as defined in claim 10 or 11, wherein said device is made of polytetrafluoroethylene.

15. A method as defined in claim 10 or 11, wherein other walls of said device not in contact with the blood are effectively non-porous to block diffusion of cellular and hormonal components.

* * * * *